(12) United States Patent
Miossec et al.

(10) Patent No.: US 11,079,391 B2
(45) Date of Patent: Aug. 3, 2021

(54) BIOLOGICAL MARKER FOR EVALUATING THE IL-17 PRO-INFLAMMATORY FUNCTIONAL CONTRIBUTION DEPENDENT LEVEL IN AN INDIVIDUAL

(71) Applicants: HOSPICES CIVILS DE LYON, Lyons (FR); UNIVERSITE CLAUDE BERNARD LYON 1, Villeurbanne (FR)

(72) Inventors: Pierre Miossec, Bron (FR); Ndieme Thiam, Lyons (FR)

(73) Assignees: Hospices Civils de Lyon, Lyons (FR); Universite Claude Bernard Lyon 1, Villeurbanne (FR)

( * ) Notice: Subject to any disclaimer, the term of this patent is extended or adjusted under 35 U.S.C. 154(b) by 762 days.

(21) Appl. No.: 15/316,525

(22) PCT Filed: Jun. 5, 2015

(86) PCT No.: PCT/IB2015/054268
§ 371 (c)(1),
(2) Date: Dec. 6, 2016

(87) PCT Pub. No.: WO2015/186106
PCT Pub. Date: Dec. 10, 2015

(65) Prior Publication Data
US 2017/0176456 A1    Jun. 22, 2017

(30) Foreign Application Priority Data
Jun. 6, 2014    (FR) .................................. 14 55152

(51) Int. Cl.
*G01N 33/68* (2006.01)
*G01N 33/50* (2006.01)
*G01N 33/53* (2006.01)
*G01N 33/563* (2006.01)

(52) U.S. Cl.
CPC ..... *G01N 33/6869* (2013.01); *G01N 2500/10* (2013.01); *G01N 2800/50* (2013.01); *G01N 2800/52* (2013.01); *G01N 2800/7095* (2013.01)

(58) Field of Classification Search
None
See application file for complete search history.

(56) References Cited

FOREIGN PATENT DOCUMENTS

WO    WO-2012059598 A2 *    5/2012    .......... A61K 31/519

OTHER PUBLICATIONS

BD Cytometric Bead Array, Human Inflammatory Cytokines Kit, Instruction Manual, pp. 1-36 (Year: 2008).*
Miossec et al., Nature Reviews Drug Discovery, vol. 11, pp. 763-776. (Year: 2012).*
Chaubad et al., Arthritis & Rheumatism, vol. 42, No. 5, pp. 963-970. (Year: 1999).*
Fossiezetal., J. Exp. Med., vol. 183, pp. 2593-2603. (Year: 1996).*
Hot et al. (Annals of the Rheumatic Diseases 71(5)768-776). (Year: 2012).*
DeFoge et al. 2010 (Journal of Immunological Methods 362:70-81) (Year: 2010).*

* cited by examiner

*Primary Examiner* — Gary B Nickol
*Assistant Examiner* — Jegatheesan Seharaseyon
(74) *Attorney, Agent, or Firm* — W & C IP

(57) ABSTRACT

The invention relates to an in vitro process for determining the functional IL-17 pro-inflammatory dependent level (IPDL) of a biological sample, comprising the following steps:
a) measuring the level of an inflammatory marker produced by IL-17-sensitive cells incubated in the presence of a biological sample,
b) measuring the level of said inflammatory marker produced by said cells incubated in the presence of a biological sample, in the presence of antibodies which neutralize the biological activity of IL-17, and
c) determining the IPDL level, which is the difference between the level of said inflammatory marker measured in step a) and the level of said inflammatory marker measured in step b).

18 Claims, 7 Drawing Sheets

Figure 1:
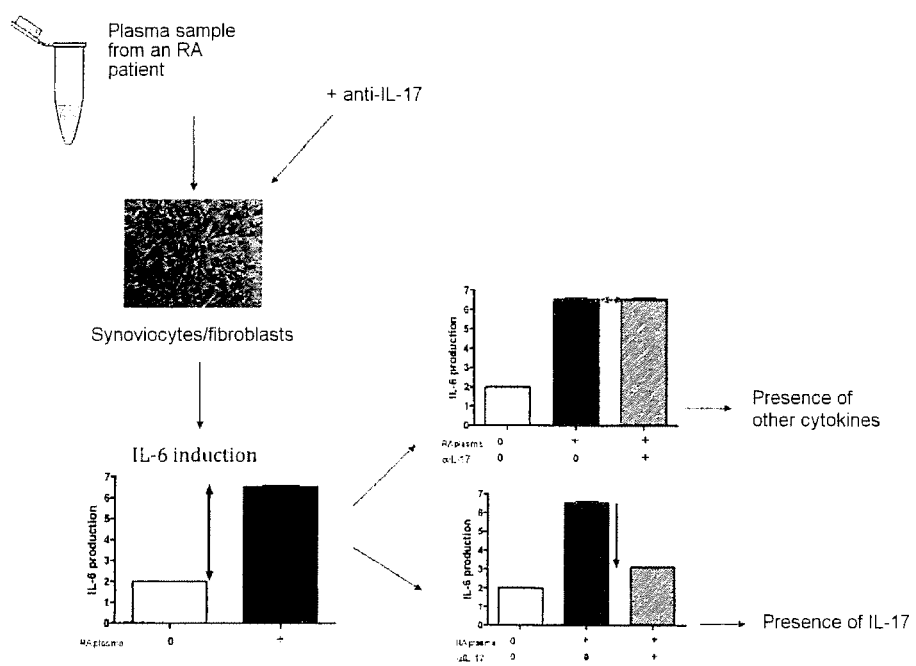

BIOLOGICAL MARKER FOR EVALUATING THE IL-17 PRO-INFLAMMATORY FUNCTIONAL CONTRIBUTION DEPENDENT LEVEL IN AN INDIVIDUAL

FIELD OF THE INVENTION

The present invention relates to identification of a novel biological marker for evaluating the IL-17 pro-inflammatory dependent functional contribution level in an individual, using a complex biological sample from said individual. The invention describes a process for determining the level of this novel marker, and diagnostic and therapeutic applications thereof.

PRIOR ART

Rheumatoid arthritis is a chronic inflammatory degenerative disease characterized by involvement of the joints which is often bilateral and symmetrical, progressing via attacks toward deformation and destruction of the affected joints. Symptomatic treatment makes use of nonsteroidal anti-inflammatories and corticosteroids. Nowadays, methotrexate is the reference treatment. "Fundamental" treatments for the disease are actively sought, in particular by identification of the cytokines involved in the inflammatory process of the disease. These treatments call for specific inhibitors of the cytokines involved. Mention may in particular be made of ETANERCEPT® and INFLIXIMAB®, which are TNF (Tumor Necrosis Factor) inhibitors. Other treatments use interleukin antagonists such as IL-1 inhibitors (ANAKINRA®), IL-6 receptor inhibitors (MrA®) and anti-CD20s (RITUXIMAB®). These compounds reduce the TNF-associated inflammation, and slow down the progression of the disease.

Nevertheless, a strong variation in response is observed between patients suffering from rheumatoid arthritis, who do not respond similarly to these treatments. It is in particular estimated that up to 30% of patients do not respond at all to the biotherapies listed above.

It has been shown that IL-17 plays a major role in inflammatory diseases, autoimmune diseases and cancer. Thus, this cytokine is now considered to be a potential therapeutic target for many diseases (Kolls and Linden, 2004). The major two forms of this cytokine are called IL-17A and IL-17F. IL-17A induces the production of numerous cytokines and chemokines, such as IL-6, G-CSF, IL-1$\beta$ and IL-8. In rheumatoid arthritis, IL-17 is present at the inflammation sites and acts by amplifying the inflammatory effects of other compounds such as TNF, which makes it a significant player in the physiology of the disease. However, the circulating levels of IL-17 in the plasma of patients are often very low, and a very great heterogeneity in circulating levels of IL-17 is observed between patients.

IL-17A inhibitors, in particular antibodies, have been proposed for the treatment of inflammatory diseases, and various clinical trials are ongoing (Miossec and Kolls, 2012). The first results obtained indicate that it is difficult to predict what the response of patients will be to these treatments, since there is a very strong individual variation. It appears that, in some patients, the role of IL-17 in the inflammatory phenomenon is considerable, whereas in others it is very weak. A major effort must now be brought to the preselection of patients whose inflammatory condition is directly dependent on IL-17, since it is these patients who would benefit from this type of treatment.

It is therefore important, from a clinical point of view, to identify a marker, other than the circulating level of IL-17 measured by ELISA in the plasma, which makes it possible to determine the size of the functional role of IL-17 in the physiology and progression of the disease in a given patient. Indeed, simply measuring the level of circulating IL-17 in the plasma of a patient does not make it possible to deduce the functional significance of IL-17 in the inflammatory phenomenon observed in said patient.

A process has been proposed for determining the level of functional IL-17 in supernatants from synovial tissues, taken from patients suffering from rheumatoid arthritis or osteoarthritis, and then placed in culture. This process comprises a step of incubating said IL-17-secreting synovial tissues in the presence of anti-IL-17 antibodies (Chabaud et al., 1999). Such an in vitro process does not resemble a determination of the level of functional IL-17 in biological samples taken from patients.

There is, at the current time, no marker for quantifying the functional part of IL-17 in an inflammatory process using a complex biological sample, and therefore determining the diseases and the individuals most able to be effectively treated with IL-17 inhibitors.

Moreover, studies have shown that patients suffering from chronic inflammatory diseases, such as rheumatoid arthritis, have a higher risk of occurrence of a cardiovascular event than the general population (Turesson et al., 2007). As it happens, at the current time, there is no known test for predicting the patients most at risk from a cardiovascular point of view, among patients suffering from a chronic inflammatory condition.

SUMMARY OF THE INVENTION

The present invention describes a process for determining, in vitro, the functional IL-17 pro-inflammatory dependent level (IPDL) of a biological sample from an individual. This process makes it possible to determine, using a complex biological sample such as a plasma sample taken from a patient, comprising other cytokines and in particular TNF, what the "functionally active" portion of IL-17 in the inflammatory phenomenon observed in said patients. This IPDL marker makes it possible to demonstrate the actual "bioavailability" of human IL-17 in the presence of numerous other cytokines and growth factors, optimizing or inhibiting the activity of IL-17, in a sample, when this sample is brought into contact with target cells in vitro.

The present invention therefore relates to a process for determining the functional IL-17 pro-inflammatory dependent level (IPDL) of a biological sample chosen from whole blood, plasma, serum, synovial fluid, cerebrospinal fluid, pleural fluid and peritoneal fluid, comprising the following successive steps:

a) measuring the level of an inflammatory marker produced by IL-17-sensitive cells, incubated in the presence of this biological sample, b) measuring the level of said inflammatory marker produced by said cells incubated in the presence of this same biological sample, in the presence of antibodies which neutralize the biological activity of IL-17, and c) determining the IPDL value, which is the difference between the level of said inflammatory marker measured in step a) and the level of said inflammatory marker measured in step b).

The knowledge of this novel IPDL marker allows in particular the following diagnostic applications:

determining the chances of response by a patient suffering from a chronic inflammatory condition to a treatment comprising the administration of an anti-IL17 antibody;

determining the efficacy of a treatment of a chronic inflammatory condition in an individual, in particular when said treatment consists of the administration of a composition comprising an IL-17-inhibiting active ingredient;

determining the risk of bone destruction in an individual suffering from a chronic inflammatory condition, in particular rheumatoid arthritis; and determining the risk of occurrence of a cardiovascular event in an individual suffering from a chronic inflammatory condition; and in vivo screening for compounds which are potentially IL-17 inhibitors, in a nonhuman animal.

The present invention also relates to a kit that is of use for determining the IL-17 pro-inflammatory dependent level of a biological sample taken from an individual, comprising:
a) an immunological test for quantifying an inflammatory marker,
b) an anti-IL-17 antibody, and
c) an immortalized line of IL-17-sensitive synovial cells.

FIGURES

FIG. 1: Development of the test intended to measure the IPDL

Schematic representation of the various steps of the process according to the invention. "RA patient" denotes a patient suffering from rheumatoid arthritis.

Figure 2:
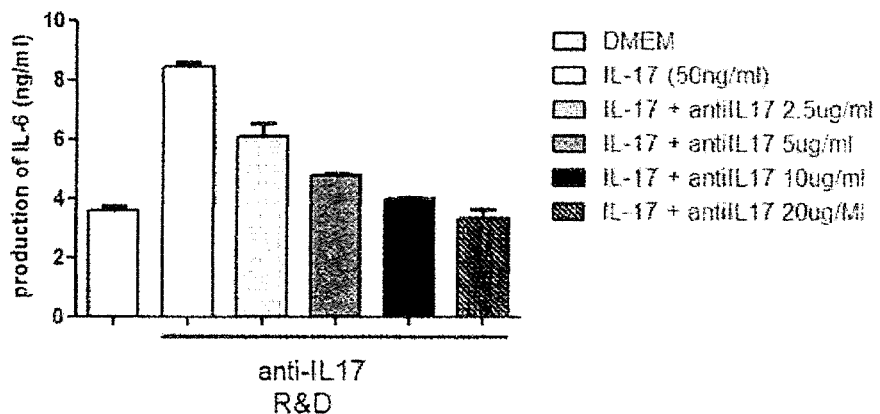

FIG. 2: Secretion of IL-6 by synoviocytes/fibroblasts from patients suffering from rheumatoid arthritis (RA FLS), stimulated with recombinant IL17, with and without anti-IL17 antibodies The cells are treated with human recombinant interleukin-17 at 50 ng, with or without anti-IL17 antibodies, at doses of 20, 10, 5 or 2.5 µg/ml. The production of IL-6 in ng/ml is measured by ELISA.

Figure 3:
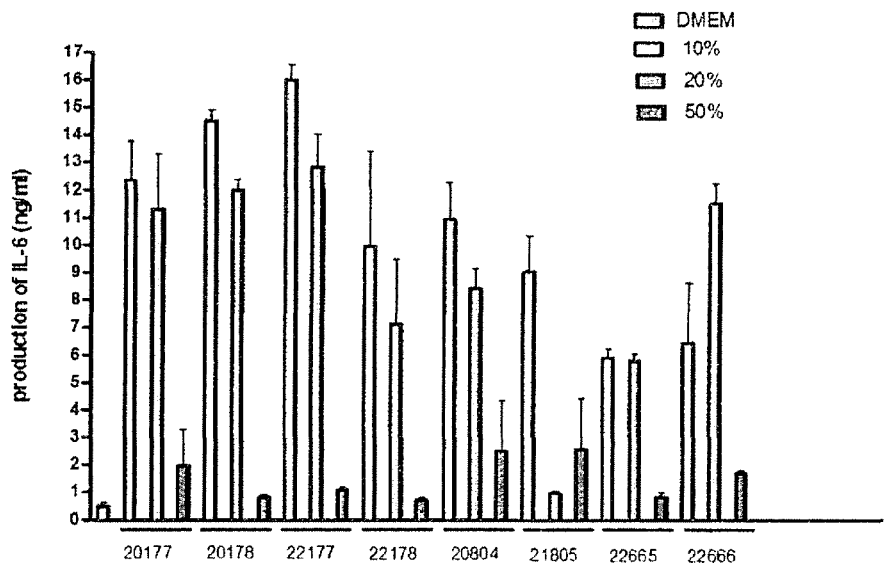

FIG. 3: Determination of the best plasma concentration for the test

The cells were treated with plasma samples from 8 patients suffering from rheumatoid arthritis, at various concentrations (50%, 20% and 10%), the level of IL-6 produced by the cells was measured by ELISA. The negative control (bar right on the left of the graph) is the use of DMEM culture medium without the addition of plasma for the incubation of the cells.

Figure 4:
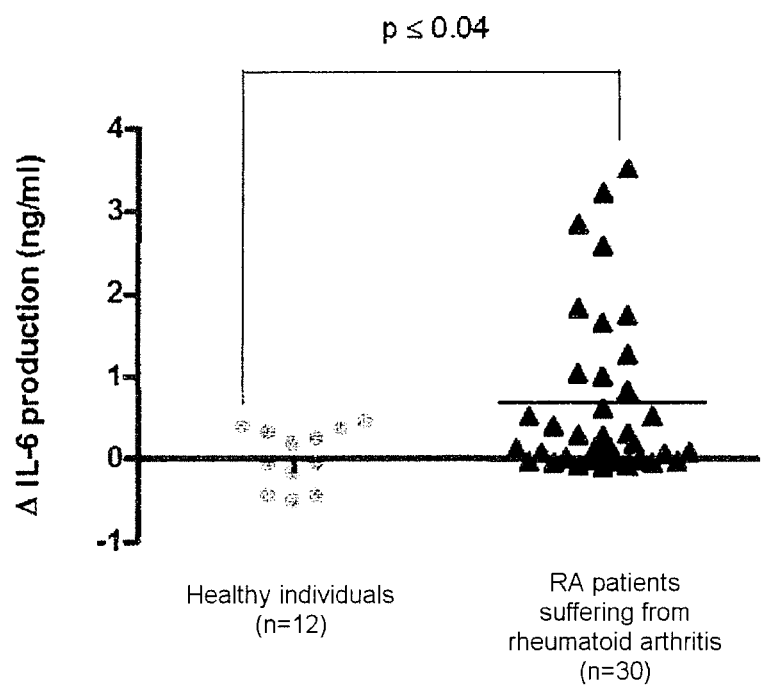

FIG. 4: Determination of the IPDL in patients suffering from rheumatoid arthritis and in healthy donors 10 000 fibroblast-like synoviocytes (FLSs) were cultured in 96-well plates in 200 µl of DMEM medium, and then the cells were treated with a plasma sample from patients at 10%, with or without anti-IL17 antibodies at 10 µg/ml. The anti-IL17 antibodies and the plasma were incubated together for 1 h before addition to the FLS cells. The cell supernatants were collected and the IL-6 production was measured by ELISA. ΔIL-6 (ng/ml) represents the IL-6 production before and after the addition of anti-IL17 antibodies. The control points are carried out with cells treated with plasma (10% v/v) from individuals in good health. Plasma from RA patients (n=23); plasma from healthy individuals (n=11).

Figure 5:
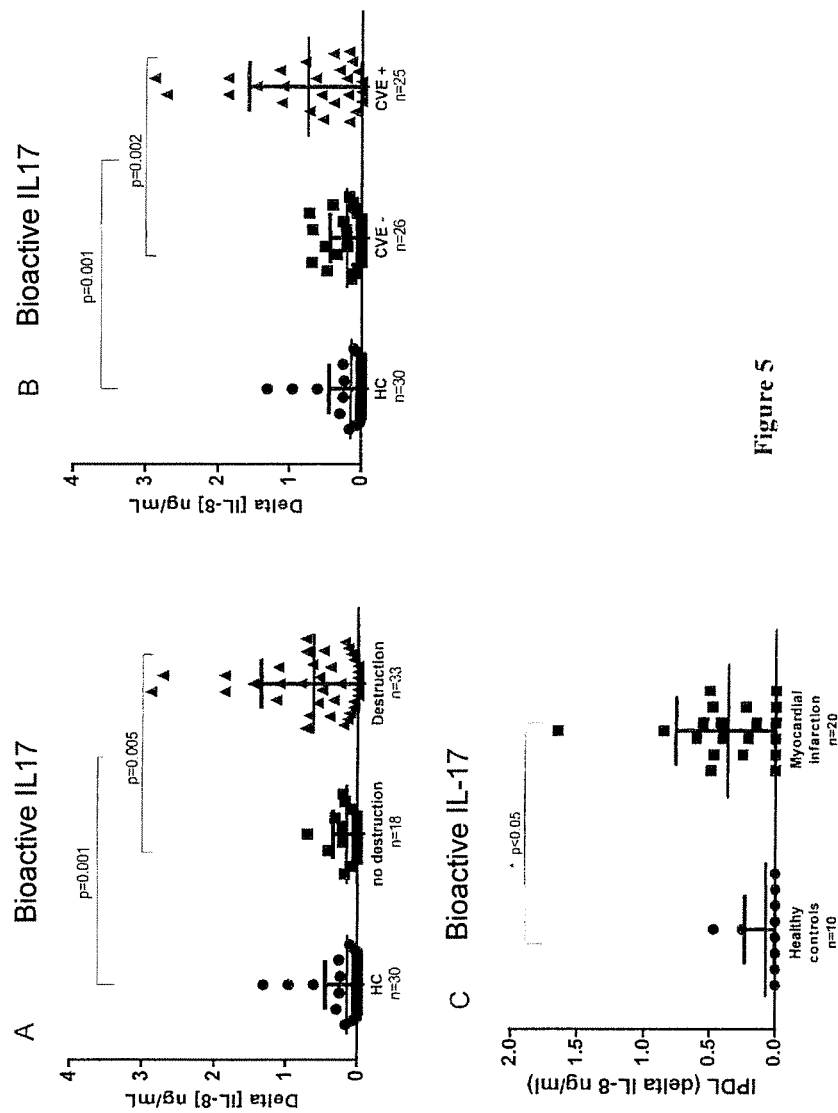

FIG. 5: Determination of the IPDL in healthy donors and patients suffering from rheumatoid arthritis (A) exhibiting bone destruction (Destruction) or no bone destruction (No Destruction), and (B) having experienced (CVE+) or not experienced (CVE−) a cardiovascular event; (C): determination of the IPDL in patients suffering from a myocardial infarction 10 000 endothelial cells (HUVECs) were cultured in 96-well plates in 200 µl of EG-M2 medium, and the cells were then treated with 10% v/v of plasma from patients suffering from rheumatoid arthritis (RA) or from healthy individuals (HC) or from patients in the acute phase of a myocardial infarction (MI); with or without anti-IL17 antibodies at 10 µg/ml. The anti-IL17 antibodies and the plasma were incubated together for 4 h before addition to the HUVEC cells. The cell supernatants were collected and the IL-8 production was measured by ELISA. ΔIL 8—production (ng/ml) represents the IL-8 production, with or without addition of anti-IL17 antibodies.

A—RA no destruction (n=18); RA destruction (n=33), HC: Healthy Controls, i.e. healthy individuals (n=30).

B—RA plasma CVE− (n=26), RA plasma CVE+ (n=25), HC: Healthy Controls, i.e. healthy individuals (n=30).

C—HC: Healthy Controls, i.e. healthy individuals (n=10); MI: patients suffering from a myocardial infarction (n=20).

Figure 6:
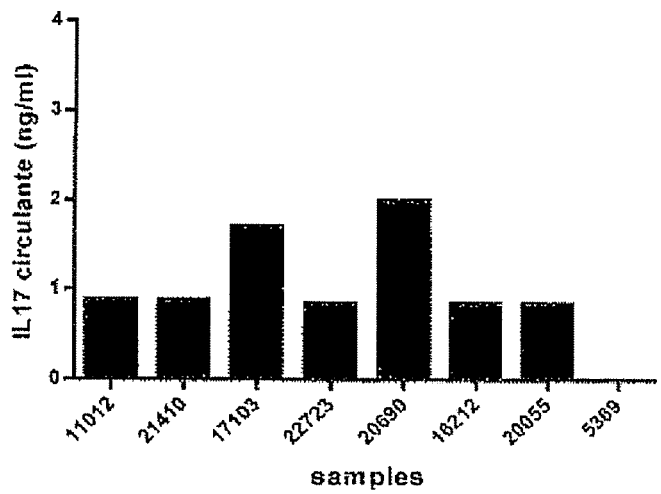
Figure 6:
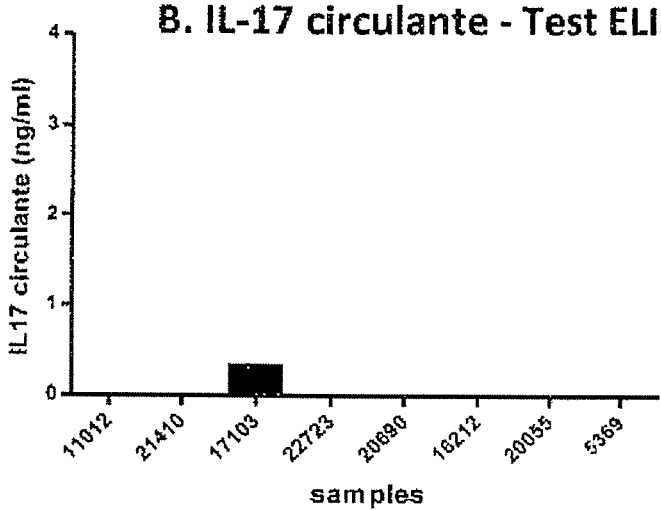
Figure 6:
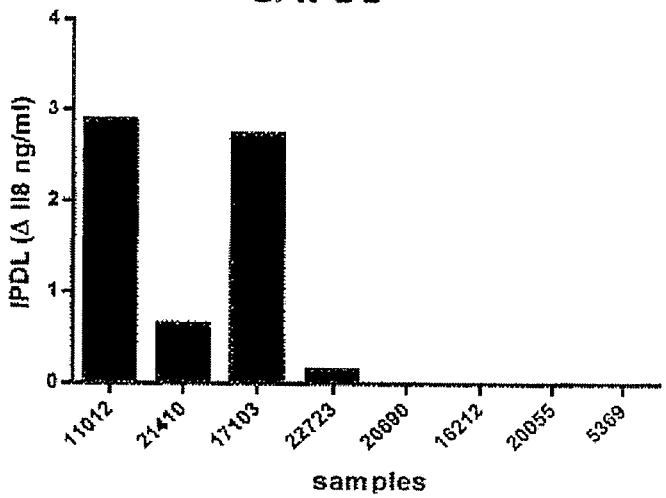

FIG. 6: Comparison of the level of circulating IL-17 and of the IPDL in the plasma from eight patients In the samples taken (samples), the IL-17 level is measured by means of two ELISA assays (A—ELISA from Dendritics®; B—ELISA from R&D Systems®). The IPDL is then measured on these same samples by stimulation of endothelial cells, and measurement of IL-8 secretion in the presence or absence of anti-IL-17 antibodies (C).

Figure 7:
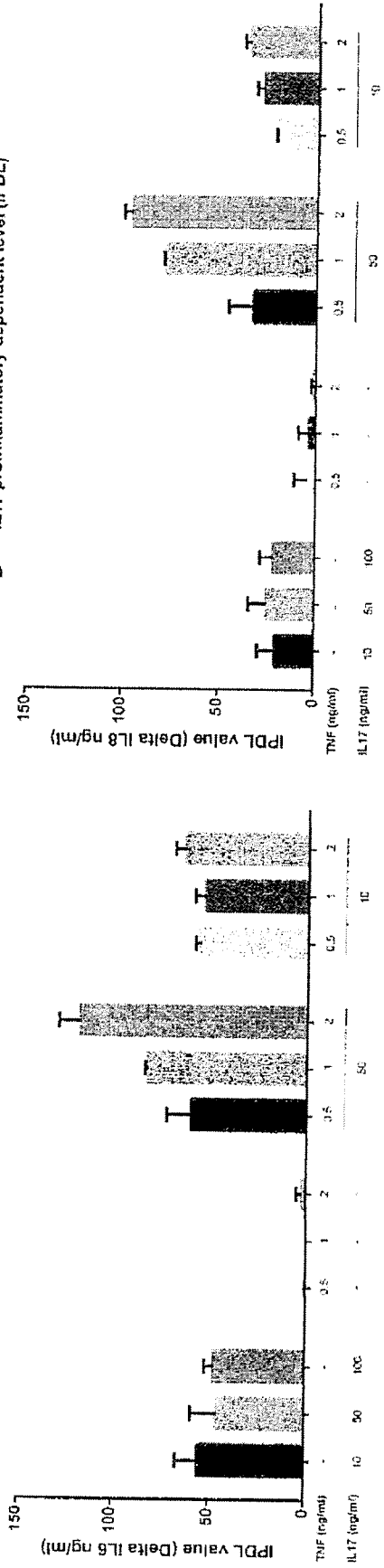
Figure 7:
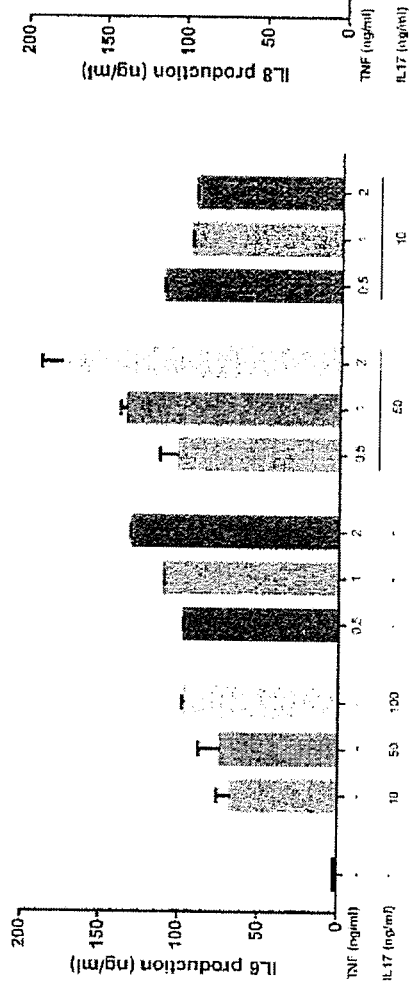

FIG. 7: Cooperation of IL-17 and TNF in synoviocyte stimulation

The production of IL-6 (A and B) and of IL-8 (C and D) by synoviocytes, stimulated with recombinant IL-17 and/or recombinant TNF, is measured by ELISA. The IPDL is then calculated on these same cells (B and D), under the same conditions.

Figure 8:
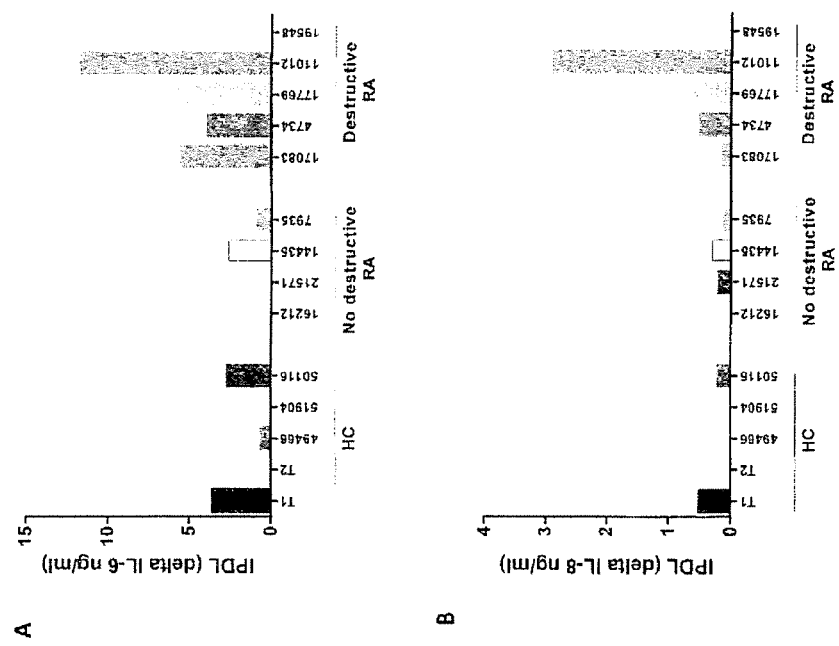

FIG. 8: Determination of the IPDL by stimulation of endothelial cells (A) and of synovial cells which have been immortalized (B)

The production of IL-6 (A) and of IL-8 (B) by IL-17-sensitive immortalized cells, respectively immortalized FLS cells (A) and HUVEC cells (B), stimulated by biological samples from patients (16212, 21571, etc.) or from healthy donors (T1, T2, 49466, etc.), according to the conditions suitable for determining the IPDL of said samples according to the process of the invention.
HC: Healthy Controls, i.e. healthy individuals; No destructive RA: patients suffering from rheumatoid arthritis, without bone destruction; Destructive RA: patients suffering from rheumatoid arthritis, with bone destruction.

DETAILED DESCRIPTION OF THE INVENTION

It has been shown according to the invention that the value of the functional IL17 pro-inflammatory dependent level (IPDL) constitutes a novel marker, independent of the "circulating IL17 level" marker, this novel marker being of use for the purposes of diagnosis and treatment of chronic inflammatory conditions, in particular of rheumatoid arthritis. It has in particular been shown that the IPDL value measured in a biological sample from a patient makes it possible to determine the capacity of said patient to react favorably to a treatment for the chronic inflammatory condition with an IL17 inhibitor, in particular with an anti-IL17 antibody.

It is also been shown that determining the value of the novel IPDL marker in a patient suffering from a chronic inflammatory condition makes it possible to evaluate the risk of cardiovascular event in this patient.

It is specified that the value of the novel IPDL marker measured in a biological sample from an individual is independent of a specific value of amount or concentration of IL17 in this sample, since, as is illustrated in the examples, a given value of IPDL, which is indicative from the diagnostic or therapeutic point of view, can be measured in samples in which varied amounts or concentrations of IL17 are measured.

The present invention relates to an in vitro process for determining the functional IL-17 pro-inflammatory dependent level (IPDL) of a biological sample chosen from whole blood, plasma, serum, synovial fluid, cerebrospinal fluid, pleural fluid and peritoneal fluid, comprising the following steps:

a) measuring the level of an inflammatory marker produced by IL-17-sensitive cells, incubated in the presence of said biological sample, b) measuring the level of said inflammatory marker produced by said cells incubated in the presence of said biological sample, in the presence of antibodies which neutralize the biological activity of IL-17, and c) determining the IPDL value, which is the difference between the level of said inflammatory marker measured in step a) and the level of said inflammatory marker measured in step b).

The present invention proposes to determine the functional contribution of IL-17 in a biological sample of complex composition, comprising multiple factors interacting with one another. Indeed, in such a sample, factors which interact with IL-17 positively, such as the cytokines TNF and IL-1 for example, and factors which interact with IL-17 negatively, inhibiting the action of IL-17, in particular such as the cytokine IL-25, are present.

The present invention proposes a process for determining the functional contribution of IL-17 within an organism, by operating under conditions that are as close as possible to the physiological conditions of said organism, in particular in the presence of the cytokines mentioned above, thereby making it possible to determine the clinical role of IL-17, and thus to evaluate the chances of response by a patient's body to a treatment based on the inhibition of IL-17.

The biological sample is taken from an individual, in particular a patient suffering from a chronic inflammatory condition, and more particularly a patient suffering from one of the disorders mentioned in the present application.

The biological activity of recombinant IL-17 is measured according to its capacity to induce the secretion of an inflammatory marker by IL-17-sensitive cells, in particular the secretion of certain interleukins by fibroblasts; this effect is completely suppressed in the presence of anti-IL-17 antibodies, thereby proving the essential role of IL-17 (Fossiez et al., 1996). This test was developed with a pure recombinant IL-17 protein, and not a complex biological sample, comprising IL-17 in the presence of numerous other factors, potentially modulators of IL-17 "bioavailability".

IL-17 or IL17 denotes interleukin-17 as identified in 1993 by the team of Rouvier et al. It was renamed IL-17A after the identification of new members of the family identified, called IL-17B to IL-17F. IL-17 is a homodimeric glycoprotein of 155 amino acids, which has a weight of 35 kDa. IL-17 is secreted by CD4+ and CD8+ lymphocytes and is involved in the coordination of local inflammation of tissues, in particular via the induction of the secretion of pro-inflammatory cytokines and inducing neutrophil mobilization (Kolls and Linden, 2004).

The present invention relates quite particularly to IL-17A, but can also be applied to other members of the family: IL-17B, IL-17C, IL-17D, IL-17E and in particular IL-17F which exhibits the highest degree of sequence identity with IL-17A, with the proviso that antibodies specifically directed against these proteins are available, and that the test is clinically relevant.

The term "Antibody which neutralizes the biological activity of IL-17" denotes an antibody which binds to IL-17 in such a way as to neutralize its biological activity. Such an antibody has the capacity to block the property of IL-17 of inducing the production of cytokines, such as IL-6 and IL-8, by IL-17-sensitive cells such as mesenchymal cells or endothelial cells. In certain cases, such an antibody blocks the activity of IL-17 by preventing the binding of IL-17 to its receptor on said sensitive cells. The invention uses in particular a neutralizing antibody directed against human interleukin 17A.

According to one particular aspect of the processes according to the invention, the inflammatory marker is advantageously chosen from IL-6, IL-8, G-CSF, GM-CSF and prostaglandin E2, and entirely preferably from IL-6 and IL-8.

Indeed IL-17 induces the secretion of pro-inflammatory factors by its numerous target cells, each type of target cell being specialized in the production and secretion of one or more cytokines or chemokines.

The expression "IL-17-sensitive cells" or "target cells" denotes cells expressing the IL-17 receptor, in particular the IL-17A receptor, and having the appropriate signaling pathway for transmitting the signal generated by the binding of the IL-17 to its receptor. Those skilled in the art know how to choose, among several cell types, those which will be most suitable for implementing the process according to the invention.

The cells are incubated, i.e. brought into contact according to a conventional protocol known to those skilled in the art, in the presence of a biological sample, optionally diluted in incubation medium suitable for the cells.

According to one particular aspect of the invention, the IL-17-sensitive cells are chosen from:
  mesenchymal cells such as synoviocytes, skin fibroblasts, and epithelial cells, and
  endothelial cells.

The mesenchymal cells are derived from the stem cells present in the mesenchyme of the embryo, which differentiate into numerous cell types. The endothelial cells make up the endothelium, their principal role being to form the wall of blood vessels.

According to one particular aspect of the invention, the target cells are fibroblast cells which secrete interleukin-6 in response to stimulation by IL-17.

The term "synoviocytes" denotes synovial membrane cells, which produce synovial fluid. They comprise in particular the "Fibroblast-Like Synoviocyte" (FLS) cells.

According to another aspect of the invention, the target cells are endothelial cells which secrete interleukin-8 in response to stimulation by IL-17.

According to one particular aspect of the invention, the biological sample on which the measurement is carried out is blood plasma, commonly called "plasma", i.e. blood from which the cells (in particular the red blood cells) have been removed by centrifugation after taking a blood sample. The plasma is the liquid part of blood in which the major components, such as the nutrients, cytokines and growth factors, bathe. This biological sample is particularly complex owing to the presence of numerous active compounds, which have multiple interactions with one another.

According to one preferred aspect of the invention, the plasma is not purified, and the sample taken is deposited as it is on the IL-17-sensitive cells in the test.

According to one particular aspect of the invention, the plasma is decomplemented, i.e. heated so as to inhibit the complement which can impair the antigen-antibody reactions; preferably, the plasma will be treated at 56° C. for 30 minutes.

The blood plasma is used in the process according to the invention to stimulate the secretion of inflammatory marker by interleukin-17-sensitive cells. The plasma can be added to the culture medium of these cells according to several modes, and in particular at various concentrations. The plasma can contain numerous cytokines (IL17, TNF, IL1, etc.) which are all capable of inducing high levels of IL-6 secretion by primary fibroblasts in culture. The use of an anti-IL-17 antibody makes it possible to determine "the proportion" or "the contribution" of IL-17 in this activation.

Preferably, the IL-17-sensitive cells are incubated, at each of steps a) and b), with a solution comprising 10% volume/volume (v/v) of plasma, i.e. a preparation containing 90% of culture medium or of incubation buffer, and 10% of plasma.

In the process according to the invention, the measurement of the level of the inflammatory marker secreted by the IL-17-sensitive cells, carried out in steps a) and b), can be carried out by any type of appropriate test, which can be easily determined by those skilled in the art. Preferably, said test will be an immunological test. According to one aspect of the invention, the marker (IL-6, IL-8 or the like, depending on the cell type) will preferably be measured by means of an immunoenzymatic test. Said test will in particular be an ELISA assay, well known to those skilled in the art, making it possible to measure the level of secretion of IL-6 or IL-8 or of another marker by means of appropriate antibodies.

According to one preferred aspect of the invention, the antibody which neutralizes the biological activity of IL-17 is a monoclonal antibody. In particular, it will be a monoclonal antibody directed against human IL-17A. This antibody may in particular be chosen from commercial antibodies. In particular, the MAB317 antibody sold by R&D Systems® is indicated for implementing the invention.

Applications of the Process of the Invention

The present invention also relates to an in vitro process for determining the chances of a patient, suffering from a chronic inflammatory condition, responding to a treatment comprising the administration of an anti-IL17 antibody, comprising the following steps:

a) determining the IPDL value of a biological sample from said individual, by means of the process as described above, and b) comparing the IPDL value obtained in step a) with a reference value.

The expression "chronic inflammatory condition" is intended to mean a health condition of an individual, in which said individual exhibits, at one or more places in the body, an inflammatory reaction, and in particular the secretion of pro-inflammatory cytokines, this being continuously over a long period of time.

The term "chances of responding" is intended to mean the probability that a treatment comprising the administration of an IL-17 inhibitor to the patient, in particular the administration of an anti-IL17 antibody to the patient, is effective, i.e. causes a decrease in or blocks the chronic inflammatory condition in said patient.

The term "biological sample from said individual" is intended to mean a sample of biological fluid taken from said individual, chosen from whole blood, plasma, serum, synovial fluid, cerebrospinal fluid, pleural fluid, and peritoneal fluid. Preferentially, this sample is blood plasma.

For the purposes of carrying out the above process, the term "reference value" is intended to mean an IPDL value measured in patients suffering from a chronic inflammatory condition, for example rheumatoid arthritis, and the response of whom to the administration of an IL-17 inhibitor, in particular the administration of an anti-IL17 antibody, is known. Generally, said reference value is a mean IPDL value measured using a biological sample from a plurality of individuals suffering from a chronic inflammatory condition, for example rheumatoid arthritis, and whose capacity to respond to the administration of an IL17 inhibitor, for example the capacity to respond to the administration of an anti-IL17 antibody, is known.

For the purposes of implementing the processes according to the invention, it is possible to choose, as "reference value", a mean IPDL value determined or measured in patients suffering from a chronic inflammatory condition, for example rheumatoid arthritis, and whose capacity to respond to a treatment with an IL-17 inhibitor, in particular to a treatment with an anti-IL-17 antibody, is known.

In certain embodiments of the process, the reference value is an IPDL value determined in "non-responder" patients, i.e. in patients in whom the administration of an IL17 inhibitor, for example an anti-IL17 antibody, does not bring about a decrease in a chronic inflammatory condition, for example a decrease in rheumatoid arthritis. In these embodiments, a patient tested according to the process of the invention will be classified as "non-responder" when the IPDL value measured for this patient is equal to or less than the reference IPDL value.

In certain embodiments of the process, the reference value is an IPDL value determined in "responder" patients, i.e. in patients in whom the administration of an IL17 inhibitor, for example an anti-IL17 antibody, brings about a decrease in a chronic inflammatory condition, for example a decrease in rheumatoid arthritis. In these embodiments, a patient tested according to the process of the invention will be classified as "responder" when the IPDL value measured for this patient is equal to or greater than the reference IPDL value.

In yet other embodiments, the reference value is an IPDL value termed a "threshold" or "cut-off" value, which is determined from IPDL values determined in "responder" patients and from IPDL values determined in "non-responder" patients. In these embodiments, a patient tested according to the process of the invention will be classified as "non-responder" when the IPDL value measured for this patient is less than the reference IPDL value. In these embodiments, a patient tested according to the process of the invention will be classified as "responder" when the IPDL value measured for this patient is greater than the reference IPDL value.

A "threshold" or "cut-off" IPDL reference value can be easily determined by those skilled in the art by means of their general knowledge. A "threshold" or "cut-off" IPDL reference value can for example be determined as described by Limmathurotsakul et al. (2011, CID, Vol. 52: 1024-1028).

According to one preferred aspect of the invention, the patients who have a chronic inflammatory condition are suffering from rheumatoid arthritis.

The present invention also relates to an in vitro process for determining the efficacy of a treatment for a chronic inflammatory condition of an individual, said treatment consisting of the administration of a composition comprising an IL-17-inhibiting active ingredient, comprising the following steps:

a) determining the IPDL value of a biological sample for said individual before the start of said treatment, by means of the process as described above, and b) determining the IPDL value of a biological sample from said individual after the start of said treatment, by means of the process as described above, it being understood that said treatment is judged to be effective when the IPDL value determined in step a) is greater than the IPDL value determined in step b).

Such a process which makes it possible to monitor the progression and/or the efficacy of a treatment corresponds to what can be referred to as a "companion test" which makes it possible to adjust or change a treatment, according to the specific response of a given individual to this treatment, during the treatment. This is particularly suitable for chronic inflammatory conditions, as observed in the rheumatoid arthritis disease, where the treatments are of long duration, and where the patient's response to a biotherapy cannot be predicted in advance.

According to one preferred aspect of the invention, said individual is suffering from rheumatoid arthritis. According to another preferred aspect of the invention, said patient is treated with monoclonal anti-IL-17 antibodies. It can be estimated that, if the treatment is effective, the "functional portion" of IL-17 in the inflammation process should be decreased following the administration of an antibody which neutralizes the activity of IL-17.

This in vitro process for determining the efficacy of a treatment for a chronic inflammatory condition of an individual with a composition comprising an IL-17-inhibiting active ingredient can also comprise the following steps:

a) determining the IPDL value of a biological sample from said individual at a first instant I1 after the start of said treatment, by means of the process as described above, and b) determining the IPDL value of a biological sample from said individual at a second instant I2, after the first instant I1, by means of the process as described above, it being understood that said treatment is judged to be effective when the IPDL value determined in step a) is greater than the IPDL value determined in step b).

According to one particular aspect of the invention, said individual is suffering from rheumatoid arthritis.

The invention also relates to an in vitro process for determining the risk of occurrence of a cardiovascular event in an individual suffering from a chronic inflammatory condition, comprising the following steps:

a) determining the IPDL value of a biological sample from said individual, by means of the process as described above, and b) comparing the IPDL value obtained in step a) with a reference value.

The term "cardiovascular event" is intended to mean any type of harmful event relating to the heart and/or blood vessels. For example, it may be a myocardial infarction.

The invention also relates to an in vitro process for determining the risk of bone destruction in an individual suffering from a chronic inflammatory condition, in particular suffering from rheumatoid arthritis, comprising the following steps:

a) determining the IPDL value of a biological sample from said individual, by means of the process as described above, and b) comparing the IPDL value obtained in step a) with a reference value.

Indeed, as is presented in example 6 and in FIGS. 5A and 5B, a link exists between the presence of a chronic inflammatory condition in an individual, and the risk of occurrence of a cardiovascular event in said individual, and the risk of observing a bone destruction.

The term "bone destruction" is intended to mean a gradual disappearance of bone tissue due to the patient's chronic inflammatory condition.

For the purposes of carrying out the process above, the term "reference value" is intended to mean an IPDL value measured in patients suffering from a chronic inflammatory condition, for example rheumatoid arthritis, and in whom the occurrence or non-occurrence of a cardiovascular event is known, or a bone destruction phenomenon has been observed. Generally, said reference value is a mean IPDL value measured using a biological sample from a plurality of individuals suffering from a chronic inflammatory condition, for example rheumatoid arthritis, and in whom the occurrence or non-occurrence of a cardiovascular event is known, or a bone destruction is observed, respectively.

For the purposes of implementing the processes according to the invention, it is possible to choose, as "reference value", a mean IPDL value determined or measured in patients suffering from a chronic inflammatory condition, for example from rheumatoid arthritis, and in whom the occurrence or non-occurrence of a cardiovascular event is known or a bone destruction is observed, respectively.

In certain embodiments of the process, the reference value is an IPDL value determined in patients who have not undergone a cardiovascular event, or do not exhibit any bone destruction. In these embodiments, a patient tested according to the process of the invention will be classified as "at reduced or zero risk of cardiovascular event" or "at reduced or zero risk of bone destruction" when the IPDL value measured for this patient is equal to or less than the reference IPDL value.

In certain embodiments of the process, the reference value is an IPDL value measured in patients having undergone a cardiovascular event, or exhibiting a bone destruction. In these embodiments, a patient tested according to the process of the invention will be classified as "at moderate or considerable risk of cardiovascular event" or "at moderate or considerable risk of bone destruction" when the IPDL value measured for this patient is equal to or greater than the reference IPDL value.

In yet other embodiments, the reference value is an IPDL value termed "threshold" value or "cut-off" value, which is determined from (i) IPDL values determined in patients "at reduced or zero risk" and (ii) IPDL values determined in patients "at moderate or considerable risk". In these embodiments, a patient tested according to the process of the invention will be classified as "at reduced or zero risk of cardiovascular event" or "at reduced or zero risk of bone destruction" when the IPDL value measured for this patient is less than the reference IPDL value. In these embodiments, a patient tested according to the process of the invention will be classified as "at moderate or considerable risk of cardiovascular event" or "at moderate or considerable risk of bone destruction" when the IPDL value measured for this patient is greater than the reference IPDL value.

A "threshold" or "cut-off" IPDL reference value can be easily determined by those skilled in the art by means of their general knowledge. A "threshold" or "cut-off" IPDL reference value can for example be determined as described by Limmathurotsakul et al. (2011, CID, Vol. 52: 1024-1028).

According to one particular aspect of the invention, said individual suffering from a chronic inflammatory condition is suffering from rheumatoid arthritis, and can be classified as "at reduced or zero risk of cardiovascular event" or "at reduced or zero risk of bone destruction" according to the IPDL measured in his or her plasma sample.

Thus, through the identification of this novel IPDL marker, it has been possible to develop the following processes for:

determining the chances of a patient, suffering from a chronic inflammatory condition, responding to a treatment comprising the administration of an anti-IL17 antibody;

determining the efficacy of a treatment for a chronic inflammatory condition of an individual, in particular when said treatment consists of the administration of a composition comprising an IL-17-inhibiting active ingredient; and determining the risk of occurrence of a cardiovascular event in an individual suffering from a chronic inflammatory condition; and determining the risk of bone destruction in an individual suffering from a chronic inflammatory condition.

It is understood that, for the implementation of all these processes, the biological sample has been taken from the individual tested, and that it is a whole blood, plasma, serum, synovial fluid, cerebrospinal fluid, pleural fluid or peritoneal fluid sample from said individual.

Said processes may be carried out on any type of IL-17-sensitive cells, but will preferably be characterized in that the IL-17-sensitive cells used are primary cultures of cells, in particular of cells taken from the individual whose biological sample is tested.

According to another aspect of the invention, the process for monitoring the efficacy of a treatment, or determining the risk of occurrence of a cardiovascular event and/or bone destruction, can be carried out on immortalized IL-17-sensitive cells. The advantage of this embodiment is that the same cell type can be used for testing biological samples from patients at various times of the treatment, and that the results will therefore be comparable.

The present invention also relates to an in vivo screening process for compounds which are potentially IL-17 inhibitors in a non-human animal, comprising the following steps:

a) determining the IPDL value of a biological sample from said animal before the start of a treatment with said compound, by means of the process according to the invention;

b) administering said candidate compound to the animal;

c) determining the IPDL value of a biological sample from said animal after the start of said treatment, by means of the process according to the invention, it being understood that said compound is judged to be effective for inhibiting IL-17 when the IPDL value determined in step a) is greater than the IPDL value determined in step c).

According to one aspect of the invention, said in vivo screening process is carried out on laboratory animals, in particular mice or rats. According to one preferred aspect of the invention, these animals have a chronic inflammatory condition. According to an even more preferred aspect of the invention, these animals are suffering from a disease equivalent to human rheumatoid arthritis, or are models for studying this disease.

Various compounds which are potentially inhibitors of IL-17, or rather of the action of IL-17, may thus be tested: antibodies, but also agents which block IL-17 receptors or neutralize the IL-17 signaling pathway. By virtue of this test making it possible to determine the IPDL before and after the start of the treatment, it will be possible to determine, in vivo, on an animal model, whether the functional contribution of IL-17 in the inflammation process has been decreased following the start of the treatment, or whether it has endured, indicating a poor efficacy of said treatment.

Step b) of administering a candidate compound will be carried out over an appropriate period for judging the efficacy of said compound, this period ranging from one day to several months, and being modeled on the usual periods of administration of compounds of this type.

Kits for Determining the IPDL

The present application also relates to a kit that is of use for determining the functional IL-17 pro-inflammatory dependent level (IPDL) of a biological sample taken from an individual, comprising:

a) an immunological test for quantifying an inflammatory marker, b) an anti-IL-17 antibody, and c) an immortalized line of IL-17-sensitive synovial cells.

In particular, the immunological quantification test will be in the form of an ELISA assay.

According to one particular aspect of the invention, said inflammatory marker is chosen from IL-6, IL-8, G-CSF, GM-CSF and prostaglandin E2, and entirely preferably from IL-6 and IL-8.

According to another particular aspect of the invention, the anti-IL-17 antibody is a monoclonal antibody.

The present application also describes a kit comprising an immortalized line of IL-17-sensitive cells, chosen from a synovial cell line, an epithelial cell line, an endothelial cell line and a fibroblast line.

In a first aspect, the kit comprises:
an ELISA assay intended for measuring the IL-6 secretion level;
an anti-IL17 antibody, in particular an anti-human IL-17A monoclonal antibody; and
an immortalized line of fibroblasts.

In a second aspect, the kit comprises:
an ELISA assay intended for measuring the IL-8 secretion level;
an anti-IL17 antibody, in particular an anti-human IL-17A monoclonal antibody; and
an immortalized line of endothelial cells.

In particular, the immortalized line of endothelial cells would be derived from the line called "HUVEC", consisting of endothelial cells from the human umbilical cord vein, these cells having been modified to create an immortalized cell line.

In one preferred aspect, the kit according to the invention comprises:
an ELISA assay intended for measuring the IL-6 secretion level;
an anti-IL17 antibody, in particular an anti-human IL-17A monoclonal antibody; and
an immortalized line of synovial cells.

According to the invention, the term "synovial cells" is intended to mean in particular cells of fibroblast type commonly called "Fibroblast-Like-Synoviocytes" (FLSs).

For example, an immortalized cell line of "Fibroblast-Like-Synoviocytes" (FLSs) can be used in the context of the invention.

EXAMPLES

Materials and Methods

Isolation and Culture of Primary Synoviocytes (of Fibroblast Type) from Patients Suffering from Rheumatoid Arthritis Synovium samples were obtained from patients suffering from rheumatoid arthritis having undergone a joint replacement.

The tissues were chopped up and digested with DNase at 0.15 mg/ml (Roche), hyaluronidase at 0.15 mg/ml (Sigma-Aldrich) and collagenase type IA at 1 mg/ml (Sigma-Aldrich) in DMEM medium (Eurobio) for one hour at 37° C. The cells were then washed and placed in culture in DMEM supplemented with 10% fetal bovine serum (Invitrogen), 200 mM of L-glutamine (Lonza), 100 U/ml of penicillin, 100 pg/ml of streptomycin (Lonza), and 5 pg/ml of plasmocin (Lonza). The synoviocytes were used at the "four-to-eight passage" stage.

Determination of the IPDL—Development of the Test on IL-17A

This test is represented diagrammatically in FIG. 1. This test was designed to determine the IPDL (IL-17 Pro-inflammatory Dependent Level) in the plasma of patients suffering from rheumatoid arthritis. Fibroblast-type synoviocytes (FLS cells) were isolated from patients and were cultured in 96-well plates in complete DMEM ($10^4$ cells/well) at 37° C./5% $CO_2$ overnight. The cells were treated with plasma (heat-decomplemented) originating from patients in serum-free DMEM for 24 h. In order to evaluate the activity associated with the circulation of IL-17A, anti-IL-17 antibodies (R & D Systems) at various concentrations (2.5, 5, 10 and 20 pg/ml) were incubated with the plasma for one hour before addition to the synoviocytes in culture. Recombinant IL-17 (R & D Systems) was used at 50 ng/ml as positive control. After 24 h, the supernatents were collected and the IL-6 was measured by ELISA.

Detection of IL-6 by ELISA

The IL-6 present in the culture supernatents was measured by ELISA (R & D Systems) according to the producer's instructions. The wells were coated with 2.0 μg/ml of antibody (anti-human IL-6) overnight at ambient temperature. After the phase of saturation with PBS buffer containing 1% of Bovine Serum Albumin (BSA) for one hour at ambient temperature, the supernatents diluted to 1/250 or the control solution were added to the wells, and incubated for 2 hours. The anti-human IL-6 antibody is added at 50 ng/ml for 2 h. Peroxidase-conjugated streptavidin diluted to 1/5000 is added to the wells and the whole thing is incubated for 20 min. The visualization is carried out by adding a solution of substrate ($H_2O_2$+TMB). The optical density is measured with a microplate reader at 450 nm.

Statistical Analysis

All the data are expressed as the mean±standard deviation. Correlations were estimated using a Graphpad Prism non-parametric 2-tailed t-test. The p values of less than 0.05 were considered to be significant.

Example 1

Human recombinant IL-17 induces IL-6 production by FLS cells and the presence of anti-IL17 antibodies at 10 μg/ml inhibits this effect.

Various concentrations of anti-IL17 antibodies are tested for blocking the effect of human recombinant IL-17 at 50 ng/ml on FLS cells; the IL-6 production by these cells was measured by ELISA. Stimulation with 50 ng/ml of recombinant IL-17 for 24 hours induces a two-fold increase in the IL-6 level in the culture supernatant. Furthermore, this experiment makes it possible to validate that the anti-IL17 antibodies inhibit the effect of IL-17 in a dose-dependent manner (FIG. 2). The anti-IL17 antibodies used at 10 μg/ml induce an almost 100% inhibition of IL-6 production. These results confirm that IL-17 induces an increase in IL-6 by the FLS cells from patients, and that the anti-IL17 antibodies at 10 μg/ml are effective.

Example 2

In this second step, several dilutions of the plasma samples from the patients were tested. For this, the FLS cells were treated with various concentrations (10%, 20% and 50% by volume) of decomplemented plasma, and the IL-6 production was measured by ELISA. Low concentrations of plasma (10% and 20%) induce a significant increase in IL-6, while high concentrations of plasma (50%) do not have a significant effect on IL-6 production (FIG. 3). This result suggests that the low concentration (10%) of plasma from patients is the favorable concentration for the subsequent experiments.

Example 3. The IPDL is Higher in Patients Suffering from Rheumatoid Arthritis than in the Healthy Donors In order to study the functional involvement of IL-17 in the pathogenesis of rheumatoid arthritis, a test was developed for determining the IPDL, the functional IL-17 pro-inflammatory dependent level, of a biological sample, in particular of blood plasma. For this, the synoviocytes or the endothelial cells were treated with 10% of plasma from patients suffering from rheumatoid arthritis and from healthy donors, in the presence or absence of anti-IL17 antibodies at 10 μg/ml. Next, the ΔIL-6 (or ΔIL-8) was measured, corresponding to the IL-6 production before and after the addition of anti-IL17 antibodies. The greater the increase in the ΔIL-6, the more "functional" is the IL-17 present in the plasma. This assay reveals that patients suffering from rheumatoid arthritis have a "ΔIL-6" or "IPDL" marker that is significantly higher than that of the healthy donors (FIGS. 4 and 5).

Thus, the presence of anti-IL17 antibodies induces a decrease in IL-6 production by the FLS cells treated with 10% of patient plasma. This observation suggests that IL-17 is present in this plasma, and that it could be functionally involved in the disease.

Example 4. Link Between IPDL and Occurrence of Cardiovascular Events (CVEs), and Bone Destruction, Observed in Patients Suffering from Rheumatoid Arthritis In order to explore the association between IPDL and complications such as the occurrence of cardiovascular events, or bone destruction, a functional biological assay was designed, using patient plasma and endothelial cells (HUVECs).

The clinical data from the patients and from the healthy donors are presented in table 1 below:

TABLE 1

| Parameters | Healthy donors (n = 30) | Patients suffering from rheumatoid arthritis | | P value |
|---|---|---|---|---|
| | | No destruction (n = 17) | Bone destruction (n = 35) | |
| Sex (M/F) | 10/20 | 7/10 | 8/27 | 0.10 |
| Age (years) | 60.1 +/− 5.5 | 66.2 +/− 10.9 | 68.9 +/− 10.9 | 0.38 |

TABLE 1-continued

| | | Patients suffering from rheumatoid arthritis | | |
|---|---|---|---|---|
| Parameters | Healthy donors (n = 30) | No destruction (n = 17) | Bone destruction (n = 35) | P value |
| Disease duration (years) | | 18.7 +/− 8.9 | 22.1 +/− 11.3 | 0.06 |

IL-8 production by HUVEC cells in the presence of samples of plasma, treated or not treated with anti-IL-17 antibodies, was measured by ELISA. The A IL8 (or IPDL) is higher in the patients suffering from rheumatoid arthritis with cardiovascular complication, than in those who have not suffered from a cardiovascular event (FIG. 5B). Furthermore, the patients exhibiting significant bone destruction have a higher IPDL compared with those not exhibiting bone destruction (FIG. 5A). Thus, a high IPDL may be correlated with a cardiovascular risk and bone destruction in a patient suffering from rheumatoid arthritis.

Interestingly, no significant difference between the patients suffering from rheumatoid arthritis without cardiovascular event or bone destruction and the healthy donors is observed; this observation confirms that not all patients suffering from rheumatoid arthritis will be sensitive to a treatment based on anti-IL-17 antibodies, since their functional IL-17 pro-inflammatory dependent level (IPDL) is not elevated, thus rendering such a treatment irrelevant.

Furthermore, a high functional IL-17 level (IPDL) was observed in patients admitted to the emergency department with a myocardial infarction. As shown in FIG. 5C, the bioactive IL-17 level is higher in the patients than in the controls (p=0.03). This reinforces our hypothesis that a high bioactive IL-17 level is a good indicator of the occurrence of acute cardiovascular events.

Example 5. Absence of Relationship Between the Amount of Circulating IL-17 and the IPDL As shown in FIG. 6, the circulating IL-17 level was measured using two different ELISA kits, originating respectively from R&D Systems® and from Dendritics®. A clear difference in results is observed with the two kits, confirming the fact that the circulating IL-17 level is not a good indicator for evaluating the pro-inflammatory level in a patient.

In parallel, the IPDL was measured on the same samples from patients—some patients exhibiting a high circulating IL-17 level with the first kit, and no IL-17 with the second kit, in particular patient 20690, do not exhibit a significant IPDL, indicating that the IL-17 present was functional.

With conflicting results for the circulating IL-17 level, the IPDL provides additional information, making it possible to distinguish plasmas containing or not containing functional IL17, and therefore patients capable of being treated with IL17 inhibitors.

Example 6. Synergistic Role of TNF and IL-17 in the Secretion of Pro-Inflammatory Cytokines/Chemokines IL-6 and IL-8 production by synoviocytes, stimulated with recombinant IL-17 and/or recombinant TNF, are measured using commercial ELISA assays. The IPDL is then calculated on these same cells, under the same conditions.

As indicated in graphs 7A and 7C, the IL-6 and IL-8 production by the synoviocytes is stimulated both by IL-17 and by TNF. Thus, when a complex biological sample is used to stimulate these cells, the respective portion of the secretion induced by the presence of IL-17 and by the presence of TNF is indissociable.

An increase in IL6 or IL8 production by the synoviocytes as a function of the IL17 concentration, or by the TNF concentration, is observed as anticipated. A synergistic effect is obtained with a simultaneous stimulation by IL17 in combination with TNF (in particular with the following values: 50 ng/ml of IL-17 and 2 ng/ml of TNF—see 7A and 7C).

The bottom two graphs (7B and 7D) demonstrate the fact that the IPDL measured, indicating the amount of "free and biologically active" IL-17, does not directly relate to the amount of recombinant IL-17 added; indeed:

in the absence of TNF, the IPDL is virtually identical whatever the concentration of IL-17 added; see the first three points of the two graphs 7B and 7D;

in the absence of IL-17, the IPDL is virtually undetectable, as expected;

in the presence of TNF, the capacity of IL-17 to stimulate the synoviocytes depends on its concentration: the IPDL is greater than that observed without TNF when the IL-17 is added in a proportion of 50 ng/ml, whereas the IPDL has a value equivalent to that observed in the presence of 10 ng/ml of IL-17 without TNF.

The IPDL is a specific measurement of "functional" IL17 since a high IPDL level, which is an indicator of the presence of functional IL-17, is observed in the presence of a combination comprising an IL17 concentration of 50 ng/ml and a high TNF concentration (from 1 to 2 ng/ml), it being possible for this situation to be observed physiologically in a plasma sample.

Moreover, the results are virtually identical when the inflammatory marker used is IL-6 or IL-8.

Example 7. Comparison of the Results Obtained on HUVEC Endothelial Cells and on FLS Immortalized Cells HUVEC endothelial cells, for which the IPDL was determined by means of measuring IL-8 as inflammatory marker, were first used in the development of the functional test.

Synovial cells of Fibroblast-Like-Synoviocyte (FLS) type, derived from patients and then immortalized, were then tested, in which cells the IPDL was determined by means of measuring IL-6 as inflammatory marker, following stimulation.

The results obtained in the endothelial cells (FIG. 8B) are, in the majority of cases, equivalent to the results obtained in the immortalized synoviocytes (FIG. 8A). The latter show higher levels on average, thereby reflecting a greater sensitivity of the immortalized synoviocytes compared with the HUVEC endothelial cells.

REFERENCES

Rouvier E, Luciani M F, Mattei M G, Denizot F, Golstein P. *CTLA*-8, *cloned from an activated T cell, bearing A U-rich messenger RNA instability sequences, and homologous to a herpesvirus saimiri gene.* J Immunol. 1993 Jun. 15; 150(12):5445-56.

Kolls J K, Linden A. *Interleukin-17 family members and inflammation.* Immunity. 2004 October; 21(4):467-76.

Miossec P, Kolls J K. *Targeting IL-17 and TH17 cells in chronic inflammation.* Nat Rev Drug Discov. October; 11(10):763-76.

Chabaud M, Durand J M, Buchs N, Fossiez F, Page G, Frappart L, Miossec P. *Human interleukin-17: A T cell-derived pro inflammatory cytokine produced by the rheumatoid synovium.* Arthritis Rheum. 1999 May; 42(5):963-70.

Turesson C, McClelland R L, Christianson T J, Matteson E L. *Severe extra-articular disease manifestations are associated with an increased risk of first ever cardiovascular events in patients with rheumatoid arthritis.* Ann Rheum Dis. 2007 January; 66(1):70-5.

Fossiez, F, Djossou O, Chomarat P, Flores-Romo L, Ait-Yahia S, Maat C, Pin J J, Garrone P, Garcia E, Saeland S, Blanchard D, Gaillard C, Das Mahapatra B, Rouvier E, Golstein P, Banchereau J, Lebecque S. *T cell interleukin-17 induces stromal cells to produce pro inflammatory and hematopoietic cytokines.* J Exp Med. 1996 Jun. 1; 183 (6):2593-603.

Limmathurotsakul D, Chantratita N, Teerawattanasook N, Piriyagitpaiboon K, Thanwisai A, Wuthiekanun V, Day N P, Cooper B, Peacock S J. *Enzyme-linked immunosorbent assay for the diagnosis of melioidosis: better than we thought.* Clin Infect Dis. 2011 Apr. 15; 52(8):1024-8.

The invention claimed is:

1. An in vitro process for determining a functional IL-17 pro-inflammatory dependent level (IPDL) of a biological sample chosen from plasma and serum, comprising the following steps:
    a) measuring a level of an inflammatory marker produced by IL-17-sensitive cells incubated in the presence of said biological sample,
    b) measuring the level of said inflammatory marker produced by said IL-17-sensitive cells incubated in the presence of said biological sample, in the presence of antibodies which neutralize biological activity of IL-17, and
    c) determining the IPDL level, which is the difference between the level of said inflammatory marker measured in step a) and the level of said inflammatory marker measured in step b).

2. The process as claimed in claim 1, said inflammatory marker being chosen from IL-6, IL-8, G CSF, GM-CSF and prostaglandin E2.

3. The process as claimed in claim 1, wherein the biological sample is a plasma sample.

4. The process as claimed in claim 3, the IL 17-sensitive cells being incubated, in each of steps a) and b), with a solution containing 10% v/v of plasma.

5. The process as claimed in claim 1, the IL-17-sensitive cells being chosen from:
    mesenchymal cells, and
    endothelial cells.

6. The process as claimed in claim 1, wherein the IL-17-sensitive cells are synoviocytes, skin fibroblasts or epithelial cells.

7. The process as claimed in claim 1, wherein the biological sample is a serum sample.

8. The process as claimed in claim 1, wherein the IL-17-sensitive cells are cells taken from an individual whose biological sample is tested.

9. The process as claimed in claim 1, the measurement of the level of said inflammatory marker being carried out, respectively in steps a) and b), by means of an immunological test.

10. The process as claimed in claim 1, the antibody which neutralizes the biological activity of IL-17 being a monoclonal antibody.

11. An in vitro process for determining the chances of a patient, suffering from a chronic inflammatory condition, of responding to a treatment comprising administering an anti-IL17 antibody, comprising the following steps:
    a) determining an IPDL value of a biological sample chosen from plasma and serum from said individual, by means of a process as claimed in claim 1,
    b) comparing the IPDL value obtained in step a) with a reference value, and
    c) determining from step b) the chances of a patient, suffering from the chronic inflammatory condition, of responding to the treatment comprising administering an anti-IL17 antibody.

12. The process as claimed in claim 11, characterized in that the IL-17-sensitive cells are cells taken from the individual whose biological sample is tested.

13. An in vitro process for determining the efficacy of a treatment for a chronic inflammatory condition of an individual, said treatment consisting of administering a composition comprising an anti-IL-17 antibody, comprising the following steps:
    a) determining an IPDL value of a biological sample chosen from plasma and serum from said individual before the start of said treatment, by means of a process as claimed in claim 1,
    b) determining the IPDL value of a biological sample from said individual after the start of said treatment, by means of the process as claimed in claim 1,
    wherein said treatment is judged to be effective when the IPDL value determined in step a) is greater than the IPDL value determined in step b), and
    c) determining from step b) the efficacy of the treatment for the chronic inflammatory condition of the individual.

14. An in vitro process for determining the efficacy of a treatment for a chronic inflammatory condition of an individual with a composition comprising an anti-IL-17 antibody, comprising the following steps:
    a) determining an IPDL value of a biological sample chosen from plasma and serum from said individual at a first instant I1 after the start of said treatment, by means of a process as claimed in claim 1,
    b) determining the IPDL value of a biological sample from said individual at a second instant I2, after the first instant I1, by means of the process as claimed in claim 1,
    wherein said treatment is judged to be effective when the IPDL value determined in step a) is greater than the IPDL value determined in step b), and
    c) determining from step b) the efficacy of the treatment for the chronic inflammatory condition of the individual.

15. An in vitro process for determining a risk of occurrence of a cardiovascular event in an individual suffering from a chronic inflammatory condition, comprising the following steps:
    a) determining an IPDL value of a biological sample chosen from plasma and serum from said individual, by means of a process as claimed in claim 1, b) comparing the IPDL value obtained in step a) with a reference value, and c) determining from step b) the risk of occurrence of the cardiovascular event in the individual suffering from the chronic inflammatory condition.

16. An in vitro process for determining a risk of bone destruction in an individual suffering from a chronic inflammatory condition, comprising the following steps:
   a) determining an IPDL value of a biological sample chosen from plasma and serum from said individual, by means of a process as claimed in claim 1,
   b) comparing the IPDL value obtained in step a) with a reference value, and
   c) determining from step b) the risk of bone destruction in the individual suffering from the chronic inflammatory condition.

17. The process as claimed in claim 1, characterized in that the IL-17-sensitive cells are immortalized cells.

18. An in vivo screening process for a candidate compound which is potentially an IL-17 inhibitor in a non-human animal, comprising the following steps:
   a) determining a IPDL value of a biological sample chosen from plasma and serum from said non-human animal before the start of a treatment with said candidate compound, by means of a process as claimed in claim 1,
   b) administering said candidate compound to the non-human animal,
   c) determining the IPDL value of a biological sample from said non-human animal after the start of said treatment, by means of the process as claimed in claim 1, wherein said candidate compound is determined to be effective for inhibiting IL-17 when the IPDL value determined in step a) is greater than the IPDL value determined in step c), and
   d) determining from step c) the efficacy of the candidate compound for inhibiting IL-17.

* * * * *